United States Patent [19] [11] 4,159,979
Fujino et al. [45] Jul. 3, 1979

[54] PROTECTED AMINO ACIDS OR PEPTIDES

[75] Inventors: Masahiko Fujino, Takarazuka; Tsunehiko Fukuda, Minoo; Chieko Kitada, Sakai, all of Japan

[73] Assignee: Takeda Chemical Industries, Ltd., Osaka, Japan

[21] Appl. No.: 897,640

[22] Filed: Apr. 18, 1978

[30] Foreign Application Priority Data

Apr. 22, 1977 [JP] Japan .................................. 52/47030

[51] Int. Cl.$^2$ ........................................... C07C 103/52
[52] U.S. Cl. ............................. 260/112.5 R; 562/430
[58] Field of Search ................... 260/112.5 R; 562/430

[56] References Cited

U.S. PATENT DOCUMENTS 3,131,174  4/1964  Schwyzer ..................... 260/112.5 R
3,926,938  12/1975  Hughes et al. ................ 260/112.5 R
3,928,306  12/1975  Uchiyama et al. ........... 260/112.5 R

OTHER PUBLICATIONS

D. Chung, et al., J. Am. Chem. Soc. 89, 1967, pp. 4208–4213.

Primary Examiner—Delbert R. Phillips
Attorney, Agent, or Firm—Wenderoth, Lind & Ponack

[57] ABSTRACT

In an amino acid having ω-amino group protected with a protective group or a peptide having the residue of such a protected amino acid, the improvement according to which the protective group is p-methylbenzylsulfonyl group. The ω-amino acids protected with p-methylbenzylsulfonyl or the peptides having residues of such protected amino acids are useful for production of various peptides by liquid phase method as well as by solid-phase method, because the protective group has specific selectivity of remaining stable under the conditions commonly employed in the removal of α-amino-protecting group but is cleaved smoothly in a good yield by hydrogen fluoride without exerting untoward influences upon peptides.

18 Claims, No Drawings

PROTECTED AMINO ACIDS OR PEPTIDES

This invention relates to a novel and useful protective group for the protection of ω-amino groups of amino acids or peptides.

In the production of a peptide, where amino acids having an ω-amino group, e.g. lysine, ornithine, α, γ-diaminobutyric acid, α, β-diaminopropionic acid or the like are among the constituent amino acid residues of the peptide, the side chain ω-amino group must be protected by means of a suitable protective group in the course of production to preclude side reactions. Moreover, an ideal protective group for this purpose must be such that it remains stable in the removal of α-amino groups which is generally performed in intermediate stages, and can be completely removed in a final stage. Nonetheless, the techniques generally practiced today for the protection of ω-amino groups fail to completely satisfy the above requirements and, rather, have a number of disadvantages. It is our impression that this is because generally the protection has been sought in the use of urethane type compounds which, by nature, offer unsatisfactory selectivity to cleave the protective groups. For example, in solid-phase synthesis, it is common practice to protect an α-amino group with t-butoxycarbonyl and an ω-amino group with carbobenzoxy but the cleavage reaction for the removal of t-butoxycarbonyl in α-position is accompanied by a cleavage, to a certain extent, of the carbobenzoxy group in ω-position which contributes to the formation of by-products such as branched peptides which, in turn, add up to fairly large proportions of impurities. In attempts to obtain improvements, 2-chlorobenzyloxycarbonyl and diisopropylmethyloxycarbonyl have been developed. However, these groups are difficult to remove completely and, in their removal with hydrogen fluoride, require a prolonged treatment or a treatment at a high temperature, thus exerting an untoward influence upon the peptide as such. All of this seems to be attributable to the poor selectivity of the urethane type of protection and, in view of this, we studied the sulfonamide type of protective groups. This invention is a result of the above studies.

One aspect of this invention is directed to an improvement on protective group for ω-amino group of an amino acid or an amino acid residue constituting peptides, the improvement according to which lies in that the protective group for ω-amino group is p-methylbenzylsulfonyl group.

Another aspect of the invention is directed to an improvement in a method for protecting ω-amino group of an amino acid or an amino acid residue in a peptide, which comprises reacting the amino acid or the peptide with a reactive derivative of a compound capable of introducing the protective group into the ω-amino group, the improvement according to which the reactive derivative is p-methylbenzylsulfonyl halide.

Further aspect of the invention is concerned with a method for cleaving the p-methylbenzylsulfonyl group protecting ω-amino group of an amino acid or an amino acid residue in a peptide with hydrogen fluoride.

The amino acids having ω-amino groups in this invention are exemplified by the amino acids mentioned above, the most prevalent one being lysine. Many peptides containing this particular amino acid are found among naturally-occurring physiologically active peptides. For example, lysine residues exist in almost all physiologically active peptides including MSH (melanophore stimulating hormone), ACTH, lysine-vasopressin, neurotensin, serum thymic factor, endorphins, substance P, thymosin α, glucagon, motilin, etc.

The amino acid which can be protected by p-methylbenzylsulfonyl according to this invention is an amino acid having an amino group at least in ω-position and, particularly, this invention is applicable, with particular advantage, to α,ω-diamino acids having an amino group in α-position as well. Where a particular amino acid has optically active forms, any of the L, D and racemic forms may be employed. For example, the protective group according to this invention is in many cases applicable with advantage to straight-chain α,ω-diamino acids containing up to 6 carbon atoms.

The carboxyl group of an amino acid having an ω-amino group protected by p-methylbenzylsulfonyl in accordance with this invention may be a free carboxyl group or a carboxyl group which has been suitably activated or protected in a conventional manner. And where an additional amino group is present in α-position, this particular α-amino group may be a free amino group or an amino group suitably protected by a conventional protective group.

The amino acid having an ω-amino group or a peptide having the residue of such amino acid protected by p-methylbenzylsulfonyl according to this invention can be produced by reacting a p-methylbenzylsulfonyl halide, preferably the corresponding chloride, with the amino acid having an ω-amino group or a peptide having the residue of such amino acid. This reaction may be conducted at a suitable temperature within the range of about −10° to 50° C. and in the presence of a solvent (e.g. water, aqueous tetrahydrofuran, aqueous dioxane, aqueous dimethylformamide, etc.)

In the case of an α,ω-diamino acid, reacting a metal complex in which α-amino group and carboxyl group are masked in a chelate formation, preferably a copper complex thereof with a p-methylbenzylsulfonyl halide yields the metal complex of α,ω-diamino acid having its ω-amino group protected by the above protective group and this latter compound can be converted to the ω-protected amino acid having a free α-amino group and a free carboxyl group upon removal of the metal in a per se conventional manner (e.g. treatment with hydrogen sulfide or a resin). If desired, the free α-amino group of this last-mentioned compound may be protected with a known protective group (e.g. t-butoxycarbonyl, carbobenzoxy, etc.) in a routine manner. It is also possible to protect the free carboxyl group of the same compound with a known protective group (e.g. metal salt, lower alkyl ester, etc.) or activate it by a conventional procedure (e.g. acid anhydride, azide, active ester, etc.).

The above-mentioned amino acid having an ω-amino group protected by p-methylbenzylsulfonyl according to this invention may be employed with remarkable advantage in the processes known per se for the production of peptides containing residues of such amino acid. The protective group according to this invention can be easily removed, for example by treatment with hydrogen fluoride at about −20°C. for one hour.

The amino acids having ω-amino groups protected by p-methylbenzylsulfonyl and the peptides containing residues of such protected amino acids, both provided by this invention, have the following and other useful features, by taking advantage of which peptides can be profitably produced in manners known per se in the art of peptide synthesis.

(1) The protective group (p-methylbenzylsulfonyl) can be removed by an expedient treatment (e.g. treatment with hydrogen fluoride) in a short period of time and almost quantitatively.

(2) The protective group has specific selectivity, and withstands and remains stable without being decomposed under the conditions normally employed at various intermediate stages in the synthesis of peptides, for example the conditions commonly employed in the removal of t-butoxycarbonyl which is an α-amino-protecting group (e.g. treatment with trifluoroacetic acid, trifluoroacetic acid-dichloromethane or 2N-HCl-dioxane, etc.) and the conditions of catalytic reduction for the removal of carbobenzoxy and benzyl ester-group.

(3) The protective group can be used with equal advantage in the liquid-phase processes as well as in the solid-phase processes.

(4) Peptides can be produced in high purity and high yield.

The conventional procedures for protecting and activating the aforementioned amino and carboxyl groups and the routine procedures for the synthesis of peptides are described, for example in J. P. Greenstein and M. Winitz, "Chemistry of the Amino Acids", Volume 2 (1961), John Wiley & Sons, Inc., New York, U.S.A. and Schröder and Lübke, "The Peptides", Vol. 1 (1966), Academic Press, New York, U.S.A.

In this specification, some of the abbreviations adopted by IUPAC-IUB Commission on Biological Nomenclature or the trivial abbreviations commonly employed in the art are sometimes employed in connection with amino acids, peptides, protective groups, active groups, etc. The following are examples of such abbreviations.

| Boc | : t-Butoxycarbonyl |
|---|---|
| Z | : Carbobenzoxy |
| 2-Cl-Z | : 2-Chlorobenzyloxycarbonyl |
| Xys | : p-Methylbenzylsulfonyl (p-xylyl-α-sulfonyl) |
| HONb | : N-Hydroxy-5-norbornene-2,3-dicarboxyimide |
| OSu | : N-Hydroxysuccinimide ester |
| ONP | : p-Nitrophenyl ester |
| OBzl | : Benzyl ester |
| Bzl | : Benzyl ether |
| OBu$^t$ | : t-Butyl ester |
| MBS | : p-Methoxybenzenesulfonyl |
| PCC | : Dicyclohexylcarbodiimide |
| Lys | : Lysine |
| Gly | : Glycine |
| Glu | : Glutamic acid |
| Leu | : Leucine |
| Tyr | : Tyrosine |
| Asn | : Asparagine |
| Pro | : Proline |
| Arg | : Arginine |
| Ile | : Isoleucine |
| Ala | : Alanine |
| Ser | : Serine |
| pGlu | : Pyrroglutamic acid |

In the examples, where amino acids have optical isomers, L-compounds are implied unless otherwise specified.

EXAMPLE 1

Synthesis of p-methylbenzylsulfonyl chloride

In a 10% aqueous solution of sodium hydroxide (250 ml) is dissolved sodium sulfite (67 g, 0.53 mol), followed by the addition of p-methylbenzyl chloride (75 g, 0.53 mol). The mixture is refluxed with stirring for 4 hours. The reaction mixture is diluted two-fold with water and filtered when hot. The filtrate is cooled. The crystals of sodium p-methylbenzylsulfonate are collected by filtration.

Yield 51 g (46%).

In dimethylformamide (90 ml) is dispersed sodium p-methylbenzylsulfonate (30 g, 0.145 mol) which is sufficientry dry. The dispersion is cooled to $-10°$ C. and under stirring, thionyl chloride (19.2 ml, 0.29 mol) is added dropwise. The mixture is stirred at room temperature for 3 hours and poured in ice-water (500 g) and extracted with ether (3 times, 150 ml each). The ethereal layers are combined, washed twice with cold water and dried over sodium sulfate. The ether is distilled off and petroleum ether is added to the crystalline residue, followed by cooling. The crystals are collected by filtration.

Yield 23.5 g (78%), m.p. 80°-81° C.

EXAMPLE 2

Synthesis of H-Lys(Xys)-OH

In a 2N-aqueous solution of sodium hydroxide (54 ml) is dissolved lysine copper complex (65 m.mol), followed by the addition of dioxane (15 ml). Under vigorous stirring at 0° C., a dioxane solution (40 ml) containing p-methylbenzylsulfonyl chloride (14.7 g, 72 m.mol) is added dropwise. After the dropwise addition has been completed, the mixture is stirred at 0° C. for one hour and at room temperature for 4 hours. The resultant precipitate is collected by filtration, washed with water and alcohol and dried. This precipitate is dispersed in 1N-hydrochloric acid and hydrogen sulfide gas is bubbled into the dispersion for about 30 minutes. Then, warm water (1 l) is added to dissolve the precipitated desired compound and the copper sulfide is filtered off. The filtrate is adjusted to pH 7 with concentrated aqueous ammonia and, after cooling, the crystals are collected by filtration and recrystallized from hot water.

Yield 8.2 g (40.7%), m.p. 261° C. (decomp.)

Rf$_1$ (n-butanol-ethyl acetate-acetic acid-water=1:1:1:1)=0.73.

$[\alpha]_D^{20} + 15.5°$ (c=0.5, acetic acid).

Elemental analysis, for $C_{14}H_{22}O_4N_2S$: Calcd.: C, 53.48; H, 7.05; N, 8.91; S, 10.20. Found: C, 53.36; H, 7.35; N, 8.86; S, 10.00.

EXAMPLE 3

Synthesis of Boc-Lys(Xys)-OH

H-Lys(Xys)-OH(6.3 g, 20 m.mols), triethylamine (4.2 ml) and 2-t-butoxycarbonyl-4,6-dimethyl-2-mercaptopyrimidine(6.2 g, 26 mmols) are reacted in a solvent mixture of water and dioxane (25 ml-25 ml) at room temperature with intense stirring for 48 hours. Following the addition of water (50 ml), the reaction mixture is extracted with ether (50 ml, twice). The aqueous layer is cooled, adjusted to pH 2 with 3N-hydrochloric acid and extracted with ethyl acetate (100 ml). The ethyl acetate layer is washed with 1N-hydrochloric acid (50 ml, 3 times) and water and dried over sodium sulfate. The ethyl acetate is distilled off and the residue is crystallized from petroleum ether by trituration. After cooling, the crystals are collected by filtration.

Yield 7.6 g (91.7%), m.p. 94°-95° C.

Rf$^2$ (chloroform-methanol-acetic acid=9:1:0.5)=0.58.

$[\alpha]_D^{20}-1.5°(c=0.5,$ methanol).

Elemental analysis, for $C_{19}H_{30}O_6N_2S$. Calcd.: C, 55.05; H, 7.30; N, 6.76. Found: C, 55.27; H, 7.09; N, 6.72.

EXAMPLE 4

Relative stability of amino-protecting groups, namely Xys, 2-chlorobenzyloxycarbonyl and Z against trifluoroacetic acid. Boc-Lys(Xys)-OH(41.4 mg, 0.1 m.mol), Boc-Lys(2-Cl-Z)-OH.t-butylamine salt (48.8 mg, 0.1 m.mol) and Boc-Lys(Z)-OH.dicyclohexylamine salt (56.1 mg, 0.1 m.mol) are each dissolved in trifluoroacetic acid (0.5 ml) containing anisole (0.03 ml) and the solutions are allowed to stand at room temperature for 24 hours. The trifluoroacetic acid is distilled off and the residue is made up to 20 ml with cold water. An aliquot of this solution is taken and its lysine content is determined by means of an amino acid analyzer. The yields of lysine (% cleavage of ε-amino-protecting groups) are calculated.

| Xys | : 0.0 % |
|---|---|
| 2-Cl-Z | : 4.8 % |
| Z | : 70.6 % |

EXAMPLE 5

Relative ease (%) of cleavage of various amino-protecting groups, namely Xys, benzylsulfonyl and 2-chlorobenzyloxycarbonyl, with hydrogen fluoride.

Boc-Lys(Xys)-OH (124.4 mg, 0.3 m.mol), $N^\epsilon$-benzylsulfonyllysine (90 mg., 0.3 m.mol) and Boc-Lys-(2-Cl-Z)-OH.t-butylamine salt (146.4 mg, 0.3 m.mol) are each treated with hydrogen fluoride (2 ml) in the presence of anisole (0.1 ml) at $-20°$ C. for one hour. After the hydrogen fluoride is distilled off, the residue is dissolved in water (50 ml). An aliquot of the solution is taken and the lysine content of the sample is determined by an amino acid analyzer. The % yields of lysine are calculated.

| Xys | : 97.3 % |
|---|---|
| Benzylsulfonyl | : 64.4 % |
| 2-Cl-Z | : 86.3 % |

EXAMPLE 6

Synthesis of H-Gly-Lys-Gly-OH (a) Preparation of Boc-Lys(Xys)-Gly-OBzl

Boc-Lys(Xys)-OH(829 mg, 2 m.mols), H-Gly-OBzl.TosOH (742 mg, 2.2 m.mols) and HONb(396 mg, 2.2 m.mols) are dissolved in acetonitrile (30 ml) and the solution is cooled to 0° C. Triethylamine (0.31 ml) and dicyclohexylcarbodiimide (454 mg, 2.2 m.mols) are added to the above solution and the mixture is stirred at 0° C. for 3 hours and at room temperature for 15 hours. The dicyclohexylurea is filtered off and the solvent is evaporated by distillation. The residue is dissolved in ethyl acetate (50 ml), washed with 5% aqueous sodium hydrogen carbonate, 1 N-hydrochloric acid and water, and dried over sodium sulfate. The solvent is distilled off and the residue is crystallized from ether. After cooling, the crystals are collected by filtration.

Yield 1.10 g (97.9%), m.p. 87°–89° C.
$[\alpha]_D^{20}-9.4°(c=0.5,$ methanol).
$Rf^2=0.59.$ Elemental analysis, for $C_{28}H_{39}O_7N_3S$. Calcd.: C, 59.87; H, 7.00; N 7.48. Found: C, 59.99; H, 6.70; N, 7.55.

(b) Preparation of Boc-Gly-Lys(Xys)-Gly-OBzl

In trifluoroacetic acid (2 ml) is dissolved Boc-Lys-(Xys)-Gly-OBzl(562 mg, 10 m.mols) and the reaction is carried out at room temperature for 20 minutes. The trifluoroacetic acid is distilled off.

The residue is treated with ether (20 ml) to obtain powders which are collected by filtration and dried. This trifluoroacetate salt and Z-Gly-ONb(370 mg, 1.0 m.mol) are dissolved in dimethylformamide (10 ml) and, after the addition of triethylamine (0.14 ml), the mixture is stirred at room temperature for one hour. The solvent is distilled off and the residue is dissolved in ethyl acetate (20 ml). The solution is washed with 5% aqueous sodium hydrogen carbonate, 1 N-hydrochloric acid and water, and dried over sodium sulfate. The solvent is distilled off and the residue is crystallized by the addition of ether. Petroleum ether is further added and, after cooling, the crystals are collected by filtration.

Yield 561 mg (86%), m.p. 70°–71° C.
$[\alpha]_D^{20}+1.34°(c=0.5,$ methanol).
$Rf^2=0.48.$ Elemental analysis, for $C_{33}H_{40}O_8N_4S$. Calcd.: C, 60.71; H, 6.18; N, 8.58; S, 4.91 Found: C, 60.71; H, 6.27; N, 8.57; S, 4.89.

(c) Synthesis of H-Gly-Lys-Gly-OH

Z-Gly-Lys(Xys)-Gly-OBzl(195 mg, 0.3 m.mol) is treated with hydrogen fluoride (3 ml) in the presence of anisole (0.3 ml) at $-20°$ C. for one hour. The hydrogen fluoride is distilled off and the residue is dissolved in water (20 ml) and extracted with ether. The aqueous layer is passed through a column of Amberlite IR-45 (acetate-form, 2×5 cm) and the column is rinsed with water (30 ml). The effluent and washings are combined and, after the addition of 1 N-hydrochloric acid (0.6 ml), lyophilized to obtain fluffy white powders.

Yield 91 mg(90.4%).
$[\alpha]_D^{20}-22.7°(c=0.5,$ 1 N-HCl).
$Rf^1=0.13.$

Elemental analysis, for $C_{10}H_{20}O_4N_4.2HCl.\frac{1}{2}H_2O$. Calcd.: C, 35.09; H, 6.77; N, 16.37 Found: C, 35.41; H, 6.70; N, 16.16.

EXAMPLE 7

Synthesis of H-Gly-Lys(Xys)-Gly-OH

Z-Gly-Lys(Xys)-Gly-OBzl(130 mg, 0.2 m.mol) is catalytically reduced in a solvent mixture of ethanol and water (15 ml-15 ml) with palladium black as the catalyst at room temperature for 3 hours. The catalyst is filtered off and the solvent is then evaporated by distillation. The crystalline residue is recrystallized from water-ethanol.

Yield 75 mg(87%), m.p. 214° C.(decomp.).
$[\alpha]_D^{20}-14.5°(c=0.5,$ acetic acid).
$Rf^1=0.61.$ Elemental analysis, for $C_{18}H_{28}O_6N_4S.\frac{1}{2}H_2O$. Calcd.: C, 49.41; H, 6.68; N, 12.80; S, 7.33. Found: C, 49.78; H, 6.81; N, 12.86; S, 6.77.

EXAMPLE 8

Synthesis of pGlu-Leu-Tyr-Glu-Asn-Lys-Pro-Arg-Arg-Pro-Tyr-Ile-Leu-OH(neurotensin)

(a) Preparation of Z-Asn-Lys(Xys)-Pro-OBzl

Boc-Lys(Xys)-OH(4.14 g, 10 m.mols), H-Pro-OBzl.HCl (2.65 g, 11 m.mols) and HONb (1.99 g, 11 m.mols) are dissolved in acetonitrile (30 ml) and the solution is cooled to 0° C. Triethylamine (1.54 ml) and dicyclohexylcarbodiimide (2.27 g, 11 m.mols) are added and the mixture is stirred at 0° C. for 4 hours and at room temperature for 15 hours. The dicyclohexylurea is filtered off and the solvent is evaporated by distillation. The residue is dissolved in ethyl acetate (100 ml), washed with 5% aqueous sodium hydrogen carbonate, 1 N-hydrochloric acid and water and dried over sodium sulfate. The ethyl acetate is then distilled off, whereupon Boc-Lys(Xys)-Pro-OBzl is obtained as a syrupy substance. (5.9 g, 98%; Rf$^1$=0.82)

This syrup is dissolved in trifluoroacetic acid (30 ml) and allowed to stand at room temperature for 30 minutes. Following the addition of 6.5 N-HCl-dioxane (2 ml), the trifluoroacetic acid is distilled off. The oil residue is triturated well with ether (50 ml) and petroleum ether (50 ml) and the supernatant is discarded. This operation is repeated for a total of 3 times and the residue is dried in the presence of sodium hydroxide. This trifluoroacetate salt, Z-Asn-OH(2.61 g, 10 m.mols) and HONb(2.07 g, 11.5 m.mols) are dissolved in dimethylformamide (30 ml) and, after cooling to 0° C., triethylamine (1.4 ml) and dicyclohexylcarbodiimide (2.38 g, 11.5 m.mols) are added. The mixture is stirred at 0° C. for 3 hours and at room temperature for 15 hours. The precipitate is filtered off and the solvent is evaporated by distillation. The residue is purified by column chromatography on silica gel (6×15 cm) using 3% methanol-chloroform as the developing solvent. The 500 ml to 640 ml fractions are pooled, the solvent is distilled off, the residue is treated with petroleum ether and the powders are collected by filtration.

Yield 2.7 g (36%), m.p. 75°–78° C.
[α]$_D^{20}$ −33.4°(c=0.5, dimethylformamide).
Rf$^1$=0.58.
Elemental analysis, for C$_{38}$H$_{47}$O$_9$N$_5$S. Calcd.: C, 60.86; H, 6.32; N, 9.34; S, 4.28. Found: C, 60.71; H, 6.24; N, 9.14; S, 4.17.

(b) Preparation of H-Asn-Lys(Xys)-Pro-OH

Z-Asn-Lys(Xys)-Pro-OBzl(2.25 g, 3 m.mols) is dissolved in a solvent mixture of ethanol and water (70 ml-40 ml) and catalytic reduction is carried out at room temperature using palladium black as the catalyst for 4 hours. The catalyst is filtered off and the solvent is then evaporated by distillation. To the residue is added acetonitrile (50 ml) and the resultant powders are collected by filtration.

Yield 1.39 g (89%), m.p. 108° C. (decomp.).
[α]$_D^{20}$ −38.7°(c=0.5, acetic acid).
Rf$^1$=0.63.
Elemental analysis, for C$_{23}$H$_{35}$O$_7$N$_5$S Calcd.: C, 52.55; H, 6.71; N, 13.33; S, 6.10. Found: C, 52.65; H, 6.88; N, 12.75; S, 5.92.

(c) Preparation of Boc-Glu(OBzl)-Asn-Lys(Xys)-Pro-OH

Boc-Glu(OBzl)-OH(1.01 g, 3 m.mols) and HONb (537 mg, 3 m.mols) are dissolved in acetonitrile (20 ml) and, after the solution is cooled to 0° C., dicyclohexylcarbodiimide (618 mg, 3 m.mols) is added. The mixture is stirred at 0° C. for 3 hours and at room temperature for 5 hours. The precipitated dicyclohexylurea is filtered off and the solvent is evaporated by distillation to obtain Boc-Glu(OBZl)-ONb. (Hereinafter, the active HONb esters of Boc-amino acids are prepared in the same manner as above)

H-Asn-Lys(Xys)-Pro-OH(1.39 g, 2.67 m.mols) is dissolved in dimethylformamide (40 ml). After triethylamine (0.38 ml) and the above Boc-Glu(OBzl)-ONb is added, the mixture is stirred at room temperature for 20 hours. The solvent is distilled off and the residue is dissolved in 5% aqueous sodium hydrogen carbonate (80 ml) and extracted with ethyl acetate (40 ml×2). The aqueous layer is cooled, adjusted to pH 2 with 3 N-hydrochloric acid and extracted with ethyl acetate-n-butanol (100 ml-20 ml). The organic layer is washed with water, dried over sodium sulfate and concentrated to about 15 ml. To the concentrate is added ether (60 ml) and, after cooling, the precipitate is collected by filtration.

Yield 1.55 g (69%), m.p. 124° C.(decomp.).
[α]$_D^{20}$ −23.9°(c=0.5, dimethylformamide).
Rf$^3$ (ethyl acetate-pyridine-acetic acid-water=60:20:6:11)=0.60.
Elemental analysis, for C$_{40}$H$_{56}$O$_{12}$N$_6$S. Calcd.: C, 56.85; H, 6.68; N, 9.96; S, 3.80. Found: C, 56.70; H, 6.78; N, 9.84; S, 3.69.

(d) Preparation of Boc-Tyr-Glu(OBzl)-Asn-Lys(Xys)-Pro-OH

In trifluoroacetic acid (10 ml) is dissolved Boc-Glu(OBzl)-Asn-Lys(Xys)-Pro-OH(1.01 g, 1.2 m.mols), and the solution is allowed to stand at room temperature for 30 minutes. After the trifluoroacetic acid is distilled off, ether (30 ml) is added to the residue and the precipitate is collected by filtration, dried and dissolved in dimethylformamide (20 ml). Then, triethylamine (0.34 ml) and Boc-Tyr-OSu(570 m.mols) are added and the mixture is stirred at room temperature for 48 hours. To the reaction mixture is added a 2% aqueous solution of citric acid (100 ml) and the precipitate is extracted into n-butanol (100 ml). The n-butanol layer is washed well with water and concentrated to about 10 ml. To the concentrate is added ether (50 ml) and, after cooling, the precipitate is collected by filtration.

Yield 1.13 g (93.4%), m.p. 119°–120° C.
[α]$_D^{20}$ −22.9°(c=0.5, dimethylformamide).
Rf$^3$=0.46.
Elemental analysis, for C$_{49}$H$_{65}$O$_{14}$N$_7$S. Calcd. C, 58.37; H, 6.50; N, 9.73; S, 3.18. Found: C, 58.29; H, 7.14; N, 9.61; S, 3.16.

(e) Preparation of Boc-Leu-Tyr-Glu(OBzl)-Asn-Lys(Xys)-Pro-OH

In trifluoroacetic acid (5 ml) is dissolved Boc-Tyr-Glu-(OBzl)-Asn-Lys(Xys)-Pro-OH(860 mg, 0.85 m.mol). The solution is allowed to stand at room temperature for 30 minutes. The trifluoroacetic acid is distilled off. Ether (30 ml) is added to the residue and the precipitate is collected by filtration, dried and dissolved in dimethylformamide (20 ml). To this solution is added triethylamine (0.24 ml) and Boc-Leu-ONb(prepared from 1.02 m.mols each of Boc-Leu-OH, HONb and DCC). The mixture is stirred at room temperature for 20 hours. To the reaction mixture is added a 2% aqueous solution of citric acid (100 ml) and the resultant precipitate is collected by filtration and rinsed well with water. It is reprecipitated from acetonitrile-ether.

Yield 824 mg(88.2%). m.p. 158°–160° C.
$[\alpha]_D^{20} -21.4°(c=0.5,$ dimethylformamide).
$Rf^3 = 0.48$.

Elemental analysis, for $C_{55}H_{76}O_{15}N_8S$. Calcd.: C, 58.91; H, 6.83; N, 9.99; S, 2.86. Found: C, 58.77; H, 7.10; N, 9.99; S, 2.71.

(f) Preparation of Z-pGlu-Leu-Tyr-Glu(OBzl)-Asn-Lys(Xys)-Pro-OH

In trifluoroacetic acid (5 ml) is dissolved Boc-Leu-Tyr-Glu(OBzl)-Asn-Lys(Xys)-Pro-OH (617 mg, 0.55 m.mol). The solution is allowed to stand at room temperature for 30 minutes. The trifluoroacetic acid is distilled off. To the residue is added ether (30 ml) and the resultant precipitate is collected by filtration and dissolved in dimethylformamide (10 ml). Triethylamine (0.16 ml) and Z-pGlu-ONb (281 mg, 0.66 m.mol) are added to the solution and the mixture is stirred at room temperature for 48 hours. To the reaction mixture is added a 2% aqueous solution of citric acid (100 ml) and the resultant precipitate is collected by filtration and washed well with water. The crude product is washed with hot acetonitrile (30 ml).

Yield 595 mg(85.4%), m.p. 209°–211° C.
$[\alpha]_D^{20} = 31.2°(c=0.5,$ dimethylformamide).
$Rf^2 = 0.43$.

Elemental analysis, for $C_{63}H_{79}O_{17}N_9S$. Calcd. C, 59.75; H, 6.29; N, 9.95; S, 2.53. Found: C, 59.48; H, 6.50; N, 9.73; S, 2.18.

(g) Preparation of Z-Arg(MBS)-Pro-OBu$^t$

Z-Arg(MBS)-OH(7.79 g, 15 m.mols) and H-Pro-OBu$^t$ (3.57 g, 15 m.mols) are dissolved in acetonitrile (100 ml). After the solution is cooled to 0° C., DCC(3.71 g, 18 m.mols) is added and the mixture is stirred at 0° C. for 5 hours and at room temperature for 15 hours. The dicyclohexylurea is filtered off and the acetonitrile is evaporated by distillation. The residue is dissolved in ethyl acetate (150 ml) and extracted with 5% aqueous sodium hydrogen carbonate, 1 N-HCl and water, followed by drying over sodium sulfate. The ethyl acetate is distilled off, ether is added to the residue, which is triturated to give crystals. The crystals are recrystallized from ethyl acetate-ether.

Yield 6.62 g (70%), m.p.107°–108° C.
$[\alpha]_D^{20} -27.5°(c=0.5,$ dimethylformamide).
$Rf^2 = 0.69$.

Elemental analysis, for $C_{30}H_{40}O_8N_5S$. Calcd.: C, 57.03; H, 6.54; N, 11.09; S, 5.08. Found: C, 57.01; H, 6.45; N, 11.13; S, 5.09.

(h) Preparation of Z-Arg(MBS)-Arg(MBS)-Pro-OBu$^t$

In methanol (100 ml) is dissolved Z-Arg(MBS)-Pro-OBu$^t$(5.05 g, 8 m.mols).

To the solution is added palladium black catalyst and hydrogen gas is bubbled into the solution for 16 hours to effect catalytic reduction. The catalyst is removed by filtration and the methanol is distilled off. The residue and Z-Arg(MBS)-OH (4.15 g, 8 m.mols) are dissolved in dimethylformamide (50 ml) and cooled to 0° C. To this is added DCC(1.98 g, 9.6 m.mols) and the mixture is stirred at 0° C. for 5 hours and at room temperature for 12 hours. The resultant precipitate is filtered off and water (300 ml) is added to the filtrate. The oily precipitate is extracted with a solvent mixture of ethyl acetate-n-butanol (200 ml-50 ml). The organic layer is washed with 5% aqueous sodium hydrogen carbonate, 1 N-hydrochloric acid and water, and dried over sodium sulfate. The solvent is evaporated to about 30 ml and ether (100 ml) is added. After cooling, precipitate is collected by filtration.

Yield 5.30 g(69.2%), m.p.119° C.(decomp.).
$[\alpha]_D^{20} -17.7°(c=0.5,$ dimethylformamide).
$Rf^2 = 0.34$.

Elemental analysis, for $C_{43}H_{59}O_{12}N_9O_2 \cdot H_2O$. Calcd.: C, 52.90; H, 6.30; N, 12.92; S, 6.57. Found: C, 53.21; H, 6.37; N, 12.92; S, 6.29.

(i) Preparation of Z-Ile-Leu-OBu$^t$

Z-Ile-ONb(6.41 g, 15 m.mols) and H-Leu-OBu$^t$(2.81 g, 15 m.mols) are dissolved in acetonitrile (30 ml) and the solution is allowed to stand at room temperature for 24 hours. The acetonitrile is distilled off and the residue is dissolved in ethyl acetate (100 ml). The solution is washed with 5% aqueous sodium hydrogen carbonate, 1 N-hydrochloric acid and water, and dried over sodium sulfate. The solvent is distilled off and the residue is crystallized from a small amount of petroleum ether. After cooling, the crystals are collected by filtration.

Yield 5.90 g(90.4%), m.p. 83°–85° C.
$[\alpha]_D^{20} -18.5°(c=0.5,$ dimethylformamide).
$Rf^2 = 0.80$.

Elemental analysis, for $C_{24}H_{38}O_5N_2$. Calcd.: C, 66.34; H, 8.81; N, 6.45. Found: C, 66.52; H, 8.97; N, 6.44.

(j) Preparation of Z-Tyr-Ile-Leu-OBu$^t$

Z-Ile-Leu-OBu$^t$(3.05 g, 7 m.mols) is dissolved in methanol (100 ml) and, after the addition of palladium black, hydrogen gas is bubbled into the solution for 3 hours to effect catalytic reduction. The catalyst is removed by filtration and the solvent is distilled off. The residue and Z-Tyr-ONb(3.81 g, 8 m.mols) are dissolved in acetonitrile (80 ml) and the solution is allowed to stand at room temperature for 24 hours. The solvent is distilled off and the residue is dissolved in ethyl acetate (100 ml). The solution is washed with 5% aqueous sodium hydrogen carbonate, 1 N-hydrochloric acid and water and dried over sodium sulfate. The ethyl acetate is distilled off and the crystalline residue is recrystallized from ethyl acetate-petroleum benzin.

Yield 3.10 g(74.2%), m.p. 142°–144° C.
$[\alpha]_D^{20} -22.2°(c=0.5,$ dimethylformamide).
$Rf^2 = 0.64$.

Elemental analysis, for $C_{33}H_{47}O_7N_3$. Calcd.: C, 66.31; H, 7.93; N, 7.03. Found: C, 66.12; H, 7.93; N, 7.05.

(k) Preparation of Z-Arg(MBS)-Arg(MBS)-Pro-Tyr-Ile-Leu-Obu$^t$

In ethanol (50 ml) is dissolved Z-Tyr-Ile-Leu-OBu$^t$ (2.09 g, 3.5 m.mols) and catalytic reduction is carried out with palladium black as the catalyst for 4 hours. The catalyst is removed by filtration and the solvent is distilled off, whereby H-Tyr-Ile-Leu-OBu$^t$ is obtained.

In trifluoroacetic acid (20 ml) is dissolved Z-Arg-(MBS)-Arg(MBS)-Pro-OBu$^t$(3.35 g, 3.5 m.mols) and the solution is allowed to stand at 0° C. for 1.5 hours. The trifluoroacetic acid is distilled off and cold water (50 ml) is added to the residue. The oily precipitate is extracted into a solvent mixture of chloroform-n-butanol(120 ml-30 ml). The organic layer is washed with water and dried over sodium sulfate. The solvent is then distilled off. To the residue is added ether (50 ml)

and the resultant powders are collected by filtration to yield Z-Arg(MBS)-Arg(MBS)-Pro-OH(3.15 g, 100%).

In dimethylformamide (50 ml) are dissolved Z-Arg(MBS)-Arg(MBS)-Pro-OH, H-Tyr-Ile-Leu-OBu$^t$ and HONb(822 mg, 4.55 m.mols). The solution is cooled to 0° C. and, then, DCC (940 mg, 4.55 m.mols) is added. The mixture is stirred at 0° C. for 5 hours and at room temperature for 15 hours. The dicyclohexylurea is removed by filtration and the solvent is distilled off. The residue is dissolved in a solvent mixture of ethyl acetate-n-butanol (120 ml-30 ml) and the solution is washed with 5% aqueous sodium hydrogen carbonate, 1 N-hydrochloric acid and water is dried over sodium sulfate. The solvent is evaporated to about 10 ml and ether (100 ml) is added. The resultant precipitate is cooled and collected by filtration. It is reprecipitated from chloroform-ethyl acetate.

Yield 3.5 g. (74.5%), m.p. 138°–141° C.
$[\alpha]_D^{20} -24.5°(c=0.5$, dimethylformamide).
Rf$^2$=0.29.
Elemental analysis, for $C_{64}H_{90}O_{16}N_{12}S_2 \cdot H_2O$. Calcd.: C, 56.28; H, 6.79; N, 12.31; S, 4.70. Found: C, 56.08; H, 6.62; N, 12.08; S, 4.52.

(l) Synthesis of pGlu-Leu-Tyr-Glu-Asn-Lys-Pro-Arg-Arg-Pro-Tyr-Ile-Leu-OH(neurotensin)

Z-Arg(MBS)-Arg(MBS)-Pro-Tyr-Ile-Leu-OBu$^t$(472 mg, 0.35 m.mol) is dissolved in a solvent mixture of ethanol-dimethylformamide (20 ml-10 ml) and, in the presence of palladium black as the catalyst, catalytic reduction is carried out by bubbling hydrogen gas into the solution at room temperature for 7 hours. The catalyst is removed by filtration and the solvent is distilled off. This residue is dissolved in dimethylformamide (10 ml) together with Z-pGlu-Leu-Tyr-Glu(OBzl)-Asn-Lys(Xys)-Pro-OH(443 mg, 0.35 m.mol) and HONb(123 mg, 0.7 m.mol) and the solution is cooled to 0° C. DCC(144 mg, 0.7 m.mol) is added and the mixture is then stirred at 0° C. for 5 hours and at room temperature for 24 hours. The precipitated dicyclohexylurea is filtered off and ethyl acetate (50 ml) is added to the filtrate. The resultant precipitate is collected by filtration. The powdery precipitate is washed with hot acetonitrile (30 ml) to yield Z-pGlu-Leu-Tyr-Glu(OBzl)-Asn-Lys(Xys)-Pro-Arg(MBS)-Arg(MBS)-Pro-Tyr-Ile-Leu-OBu$^t$.

Yield 677 mg(78.5%), m.p. 189°–190° C.
$[\alpha]_D^{20} -32.6°$ C.(c=0.5, dimethylformamide).
Rf$^3$=0.74, Rf$^1$=0.87.
Elemental analysis, for $C_{119}H_{161}O_{30}N_{21}S_3$. Calcd.: C, 58.05; H, 6.59; N, 11.95; S, 3.91. Found: C, 57.72; H, 6.66 N, 11.67; S, 3.65.

This protected tridecapeptide (482 mg, 0.196 m.mol) is crushed and treated with hydrogen fluoride (7 ml) in the presence of anisole (0.25 ml) at −20° C. for one hour. The hydrogen fluoride is distilled off and the residue is dissolved in a 5% aqueous solution of acetic acid (20 ml) and washed with ether (20 ml×2). The aqueous layer is passed through an ion exchange column of Amberlite IR-410 (acetate-form, 2×7 cm). The effluent is combined with washings (total: approx. 80 ml) and lyophilized. The resultant powders are dissolved in the upper layer of a small amount of n-butanol-acetic acid-water (4:1:5) and the solution is run onto the top of a column of Sephadex G-25(2.5×120 cm) equilibrated with the lower layer of said solvent mixture. Thereafter, the column is developed with the upper layer solution of the same solvent mixture. The flow rate is 40 ml/hour and the eluate is collected in 8 l ml-fractions. The fractions from 320 ml to 400 ml are pooled and the solvent is distilled off. The residue is dissolved in water (100 ml) and lyophilized to yield the desired product as fluffy powders.

Yield 215 mg(66%).
$[\alpha]_D^{19} -100.6°(c=0.5$, 1% aqueous acetic acid).
Rf$^4$(n-butanol-pyridine-acetic acid-water=15:10:3:12)=0.50.
Rf$^1$=0.61.
Elemental analysis, for $C_{78}H_{121}O_{20}N_{21} \cdot 3CH_3COOH \cdot 5H_2O$. Calcd.: C, 51.93; H, 7.42; N, 15.14. Found: C, 52.05; H, 7.42; N, 15.31.

Amino acid analysis: Lys 1.00; ammonia 0.93; Arg 2.13; Asp 1.10; Glu 1.93; Pro 2.24; Ile 0.94; Leu 1.87; Tyr 1.90.

EXAMPLE 9

Production of Serum thymic factor
(pGlu-Ala-Lys-Ser-Gln-Gly-Gly-Ser-Asn-OH)

The reaction cell of an automatic peptide synthesizer (Shimadzu Seisakusho, K.K. APS-800) is charged with 3 g of Boc-Asn-resin which is then swollen with dichloromethane for 12 hours. The amino acid derivatives used are Boc-Ser (Bzl)-OH, Boc-Gly-OH, Boc-Gln-OH, Boc-Lys(Xys)-OH, Boc-Ala-OH and pGlu-OH. The various amino acids were introduced in the following sequence.

Dichloromethane (3 min. × 3), 50% trifluoroacetic acid/dichloromethane (10 min. and 30 min.), dichloromethane (3 min. × 3) ethanol (3 min. × 3), chloroform (5 min. × 3), 10% triethylamine/chloroform(10 min.), chloroform (3 min. × 3), dichloromethane (3 min. × 2), Boc-amino acid-anhydride (synthesized from Boc-amino acid and DCC in a conventional manner and immediately used) (30 min. and 60 min.), acetylation (dichloromethane, triethylamine and acetic anhydrie) (10 min. × 2), dichloromethane (3 min. × 3) [Provided that Boc-Gln is introduced as Boc-Gln-ONP and coupling of pGlu-OH is conducted in DMF by using DCC]

Finally, the peptide-resin, pGlu-Ala-Lys(Xys)-Ser(Bzl)-Gln-Gly-Gly-Ser(Bzl)-Asn-resin, is washed with methanol, glacial acetic acid, dimethylformamide and ether, and dried.

Yield 3.94 g.

Hydrogen fluoride (30 ml) is introduced in a Teflon ® resin cylinder containing 3 g of the above peptide-resin and 3 ml of anisole and the contents are stirred at 0° C. for one hour. Immediately the hydrogen fluoride is distilled off under reduced pressure and the residue is extracted twice with 100 ml of water. The extract is washed 3 times with 50 ml of ether and passed through a column ($\phi$1.5 cm × 30 cm) of Amberlite IRA-410(acetate-form). The effluent is lyophilized to yield 190 mg of white powders. These powders are dissolved in a 0.1 N aqueous solution of acetic acid and gel filtration is carried out on a column ($\phi$2×150 cm) of Sephadex LH-20. Further gel filtration on a column ($\phi$2×160 cm) of Sephadex G-25 yields 110 mg of the desired nonapeptide.

Amino acid analysis (hydrolysis with 5.7 N-HCl): Lys 1.05; Asp 0.96; Glu 2.08; Ser 1.87; Gly 1.92; Ala 1.00(86% recovery).

EXAMPLE 10

Synthesis of $N^\beta$-p-methylbenzylsulfonyl-DL-$\alpha,\beta$-diaminopropionic acid DL-$\alpha,\beta$-diaminopropionic acid hydrochloride (140 mg) is dissolved in 1 N aqueous sodium hydroxide (3 ml), followed by the addition of basic copper carbonate (180 mg). The mixture is stirred at room temperature for 2 hours and insolubles are filtered off.

Dioxane (5 ml) is added to the filtrate and the mixture is cooled with ice. Under vigorous stirring, a solution of p-methylbenzylsulfonylchloride (408 mg) in dioxane (3 ml) is added dropwise, while keeping pH of the mixture above 10 by addition of 1 N aqueous sodium hydroxide. After the addition, the mixture is stirred at room temperature for 3 hours. The dioxane is distilled off and pH of the aqueous residue is adjusted to pH 2 by addition of conc. sulfuric acid. Hydrogen sulfide is bubbled into the mixture and the resulting cupric sulfide is filtered off. The filtrate is passed through an ion exchange column (1×5 cm) of Amberlite IR-120 (H+ form), which is washed with water (20 ml). The column is eluted with 1 N aqueous pyridine to eluate the desired compound and the effluent is concentrated up to about 5 ml. Resulting crystals are collected by filtration and recrystallized from hot water.

Yield: 37 mg (13.6%), m.p. 235° C. (decomp.).
$Rf^1 = 0.62$
Elemental analysis, for $C_{11}H_{16}O_4N_2S$. Calcd.: C, 48.51; H, 5.92; N, 10.29; S, 11.78. Found: C, 48.11; H, 5.80; N, 10.14; S, 11.65.

EXAMPLE 11

Synthesis of serum thymic factor (a) Synthesis of pGlu-Ala-Lys(Xys)-Ser(Bzl)-Gln-Gly-Gly-resin Boc-Gly-resin (6.0 g) is swelled with dichloromethane in the automatic peptide synthesizer (APS-800 of Shimadzu Seisakusho) for 12 hours. Each amino acid is introduced in the cycle shown in the Example 9. As to Gln and pGlu, the procedure similar to those in the Example 9 are employed. Finally resulting resin is washed with methanol, glacial acetic acid, dimethylformamide and ether and dried.

Yield: 7.0 g.

(b) Synthesis of pGlu-Ala-Lys(Xys)-Ser(Bzl)-Gln-Gly-Gly-NHNH$_2$ pGlu-Ala-Lys(Xys)-Ser(Bzl)-Gln-Gly-Gly-resin (3.6 g) is suspended in dimethylformamide (18 ml) and hydrazine hydrate (2 ml) is added. The mixture is gently stirred at room temperature for 48 hours. Resin is filtered off and the filtrate is distilled under reduced pressure. Ether is added to the residue and resulting powder is collected by filtration.

Yield: 476 mg.

The powder is chromatographed on a column (2.7×3 cm) of silica gel with ethyl acetate-pyridine-acetic acid-water (30:10:3:5) and fractions from 70 to 80 ml are pooled. The solvent is distilled off and ether is added and resulting power is collected by filtration.

Yield: 168 mg, m.p. 196°-199° C.
$Rf^3 = 0.16$, $Rf^1 = 0.51$.

Amino acid analysis (Hdrolysis with 5.7 N HCl): Lys 0.96, Ser 0.92, Glu 2.02, Gly 1.94, Ala 1.0 (average recovery 76.6%).

(c) Synthesis of serum thymic factor, pGlu-Ala-Lys-Ser-Gln-Gly-Gly-Ser-Asn-OH pGlu-Ala-Lys(Xys)-Ser(Bzl)-Gln-Gly-Gly-NHNH$_2$ (140 mg) is dissolved in dimethylformamide (5 ml). While the solution is cooled to −70° C., 6.51 N HCl-dioxane (0.05 ml) and isoamylnitrite (0.02 ml) are added. The mixture is stirred at −30° C. for 35 minutes and cooled again to −70° C., followed by addition of triethylamine (0.05 ml). HCl-H-Ser-Asn-OBu$^t$ which is prepared by reducing Z-Ser-Asn-OBu$^t$ (123 mg) is dissolved in dimethylformamide (2 ml) and this solution is added to the mixture, followed by addition of triethylamine (0.05 ml). The mixture is stirred between −15° C. and 5° C. for 30 hours. Insolubles are filtered off and the filtrate is distilled to evaporate the solvent. Ether is added and resulting powder is collected by filtration. Into a mixture of the powder and anisole contained in a cylinder of teflon resin, is introduced hydrogen fluoride (5 ml) and the mixture is stirred at 0° C. for one hour. Immediately the hydrogen fluoride is distilled off under reduced pressure and the residue is extracted twice-with water (10 ml each). The aqueous extract is washed three times with ether (3 ml each) and passed through a column (1.5×10 cm) of Amberlite IRA-410 (acetate form).

The effluent is lyophilized to yield power (170 mg). The powder is subjected to gel filtration on a column (2.2×119 cm) of Sephadex LH-20 with 0.1 N aqueous acetic acid. Fractions from 176 to 188 ml are pooled and lyophilized to yield serum thymic factor (23 mg).

$[\alpha]_D^{27} - 65.6°(c = 0.5$, water).
$Rf^4 = 0.19$ (cellulose plate).
Electrophoresis (pH 6.5, 600 V): 0.17×Arg.
(Electrophoresis of Arg: 5.4 cm).
Amino acid analysis: Lys 1.10, Asp 1.03, Ser 1.86, Glu 2.05, Gly 2.0, Ala 1.0 (average recovery 71.3%).

What is claimed is:

1. An amino acid selected from the group of lysin,e $\alpha,\beta$-diaminopropionic acid, $\alpha,\gamma$-diaminobutyric acid and ornithine having a protective group or a peptide containing the residue of such a protected amino acid, where the protective group is p-methylbenzylsulfonyl.

2. An amino acid or peptide as claimed in claim 1, wherein the amino acid is lysine.

3. An amino acid or peptide as claimed in claim 1, wherein the amino acid is $\alpha,\beta$-diaminopropionic acid.

4. An amino acid or peptide as claimed in claim 1, wherein the amino acid is $\alpha,\gamma$-diaminobutyric acid.

5. An amino acid or peptide as claimed in claim 1, wherein the amino acid is ornithine.

6. A peptide as claimed in claim 1, wherein the peptide is neurotensin.

7. A peptide as claimed in claim 1, wherein the peptide is serum thymic factor.

8. A peptide as claimed in claim 1, wherein the peptide is melanophore stimulating hormone.

9. A peptide as claimed in claim 1, wherein the peptide is ACTH.

10. A peptide as claimed in claim 1, wherein the peptide is lysine-vasopressin.

11. A peptide as claimed in claim 1, wherein the peptide is endorphin.

12. A peptide as claimed in claim 1, wherein the peptide is substance P.

13. A peptide as claimed in claim 1, wherein the peptide is thymosin α.

14. A peptide as claimed in claim 1, wherein the peptide is glucagon.

15. A peptide as claimed in claim 1, wherein the peptide is motilin.

16. In a method for protecting ω-amino group of an amino acid selected from the group of lysine, α,β-diaminopropionic acid, α,γ-diaminobutyric acid and ornithine or of such an amino acid residue in a peptide which comprises reacting the amino acid or the peptide with a reactive derivative of a compound capable of introducing the protecting group into the ω-amino group, the improvement according to which the reactive derivative is p-methylbenzylsulfonyl halide.

17. A method as claimed in claim 16, wherein the p-methylbenzylsulfonyl halide is p-methylbenzylsulfonyl chloride.

18. In a method for deprotecting the protected ω-amino group of an amino acid or an amino acid residue in a peptide which comprises reacting the protected amino acid or peptide with a protective group cleaving agent the improvement according to which the protecting group is p-methylbenzylsulfonyl and the cleaving agent is hydrogen fluoride.

* * * * *